(12) United States Patent
Pottgen et al.

(10) Patent No.: US 6,413,411 B1
(45) Date of Patent: Jul. 2, 2002

(54) METHOD AND APPARATUS FOR AMPEROMETRIC DIAGNOSTIC ANALYSIS

(75) Inventors: Paul A. Pottgen, Allison Park; Neil J. Szuminsky, Pittsburgh; Jonathan L. Talbott, Freedom; Joseph Jordan, deceased, late of State College; By Colina L. Jordan, executor, Bellefonte, all of PA (US)

(73) Assignee: Tall Oak Ventures, Pittsburgh, PA (US)

( * ) Notice: Subject to any disclaimer, the term of this patent is extended or adjusted under 35 U.S.C. 154(b) by 0 days.

(21) Appl. No.: 09/696,253

(22) Filed: Oct. 26, 2000

Related U.S. Application Data (63) Continuation of application No. 08/386,919, filed on Feb. 9, 1995, now Pat. No. 6,153,069.

(51) Int. Cl.[7] .............................................. G01N 27/26
(52) U.S. Cl. .................................. 205/777.5; 205/775
(58) Field of Search ............................... 205/775, 777.5

(56) References Cited

U.S. PATENT DOCUMENTS

| | | | | |
|---|---|---|---|---|
| 5,108,889 A | * | 4/1992 | Smith et al. ................... 435/4 |
| 5,508,171 A | * | 4/1996 | Walling et al. .......... 205/777.5 |
| 5,645,710 A | * | 7/1997 | Shieh ......................... 205/775 |
| 6,153,069 A | | 11/2000 | Pottgen et al. .............. 204/403 |

* cited by examiner

*Primary Examiner*—T. Tung
*Assistant Examiner*—Alex Noguerola
(74) *Attorney, Agent, or Firm*—Oblon, Spivak, McClelland, Maier & Neustadt, P.C.

(57) ABSTRACT

The present invention relates to a novel method and apparatus for the amperometric determination of an analyte, and in particular, to an apparatus for amperometric analysis utilizing a novel disposable electroanalytical cell for the quantitative determination of biologically important compounds from body fluids.

10 Claims, 10 Drawing Sheets

METHOD AND APPARATUS FOR AMPEROMETRIC DIAGNOSTIC ANALYSIS

This application is a of continuation Ser. No. 08/386,919 filed Feb. 9, 1995 now U.S. Pat. No. 6,153,069.

FIELD OF THE INVENTION

The present invention relates to a disposable electroanalytical cell and a method and apparatus for quantitatively determining the presence of biologically important compounds such as glucose; hormones, therapeutic drugs and the like from body fluids.

Although the present invention has broad applications, for purposes of illustration of the invention specific emphasis will be placed upon its application in quantitatively determining the presence of a biologically important compound—glucose.

With Respect to Glucose

Diabetes, and specifically diabetes mellitus, is a metabolic disease characterized by deficient insulin production by the pancreas which results in abnormal levels of blood glucose. Although this disease afflicts only approximately 4% of the population in the United States, it is the third leading cause of death following heart disease and cancer. With proper maintenance of the patient's blood sugar through daily injection of insulin, and strict control of dietary intake, the prognosis for diabetics is excellent. The blood glucose levels must, however, be closely followed in the patient either by clinical laboratory analysis or by daily analyses which the patient can conduct using relatively simple, non-technical, methods.

At present, current technology for monitoring blood glucose is based upon visual or instrumental determination of color change produced by enzymatic reactions on a dry reagent pad on a small plastic strip. These colorimetric methods, which utilize the natural oxidant of glucose to gluconic acid, specifically oxygen, are based upon the reactions:

B-D-Glucose+$O_2$+$H_2O$→D-Gluconic Acid+$H_2O_2$ $H_2O_2$+Reagent→$H_2O$+color

Wherein glucose oxidase catalyzes the conversion of B-D Glucose to D-Gluconic Acid. The hydrogen peroxide produced is measured by reflectance spectroscopic methods by its reaction with various dyes, in the presence of the enzyme peroxidase, to produce a color that is monitored.

While relatively easy to use, these tests require consistent user technique in order to yield reproducible results. For example, these tests require the removal of blood from a reagent pad at specified and critical time intervals. After the time interval, excess blood must be removed by washing and blotting, or by blotting alone, since the color measurement is taken at the top surface of the reagent pad. Color development is either read immediately or after a specified time interval.

These steps are dependent upon good and consistent operating technique requiring strict attention to timing. Moreover, even utilizing good operating technique, calorimetric methods for determining glucose, for example, have been shown to have poor precision and accuracy, particularly in the hypoglycemic range. Furthermore, instruments used for the quantitative calorimetric measurement vary widely in their calibration methods: some provide no user calibration while others provide secondary standards.

Because of the general lack of precision and standardization of the various methods and apparatus presently available to test for biologically important compounds in body fluids, some physicians are hesitant to use such equipment for monitoring levels or dosage. They are particularly hesitant in recommending such methods for use by the patients themselves. Accordingly, it is desirable to have a method and apparatus which will permit not only physician but patient self-testing of such compounds with greater reliability.

The present invention addresses the concerns of the physician by providing enzymatic amperometry methods and apparatus for monitoring compounds within whole blood, serum, and other body fluids. Enzymatic amperometry provides several advantages for controlling or eliminating operator dependant techniques as well as providing a greater linear dynamic range. A system based on this type of method could address the concerns of the physician hesitant to recommend self-testing for his patients.

Enzymatic amperometry methods have been applied to the laboratory based measurement of a number of analytes including glucose, blood urea nitrogen, and lactate. Traditionally the electrodes in these systems consist of bulk metal wires, cylinders or disks imbedded in an insulating material. The fabrication process results in individualistic characteristics for each electrode necessitating calibration of each sensor. These electrodes are also too costly for disposable use, necessitating meticulous attention to electrode maintenance for continued reliable use. This maintenance is not likely to be performed properly by untrained personnel (such as patients); therefore, to be successful, an enzyme amperometry method intended for self-testing (or non-traditional site testing) must be based on a disposable sensor that can be produced in a manner that allows it to give reproducible output from sensor to sensor and at a cost well below that of traditional electrodes.

The present invention addresses these requirements by providing miniaturized disposable electroanalytic sample cells for precise micro-aliquot sampling, a self-contained, automatic means for measuring the electrochemical reduction of the sample, and a method for using the cell and apparatus according to the present invention.

The disposable cells according to the present invention are preferably laminated layers of metallized plastic and nonconducting material. The metallized layers provide the working and reference electrodes, the areas of which are reproducibly defined by the lamination process. An opening through these layers is designed to provide the sample-containing area or cell for the precise measurement of the sample. The insertion of the cell into the apparatus according to the present invention, automatically initiates the measurement cycle.

To better understand the process of measurement, a presently preferred embodiment of the invention is described which involves a two-step reaction sequence utilizing a chemical oxidation step using other oxidants than oxygen, and an electro-chemical reduction step suitable for quantifying the reaction product of the first step. One advantage to utilizing an oxidant other than dioxygen for the direct determination of an analyte is that such other oxidants may be prepositioned in the sensor in a large excess of the analyte and thus ensure that the oxidant is not the limiting reagent (with dioxygen, there is normally insufficient oxidant initially present in the sensor solution for a quantitative conversion of the analyte).

In the oxidation reaction, a sample containing glucose, for example, is converted to gluconic acid and a reduction product of the oxidant. This chemical oxidation reaction has been found to precede to completion in the presence of an enzyme, glucose oxidase, which is highly specific for the substrate B-D-glucose, and catalyzes oxidations with single and double electron acceptors. It has been found, however, that the oxidation process does not proceed beyond the formation of gluconic acid, thus making this reaction particularly suited for the electrochemical measurement of glucose.

In a presently preferred embodiment, oxidations with one electron acceptor using ferrocyanide, ferricinum, cobalt (III) orthophenanthroline, and cobalt (III) dipyridyl are preferred. Benzoquinone is a two electron acceptor which also provides excellent electro-oxidation characteristics for amperometric quantitation.

Amperometric determination of glucose, for example, in accordance with the present invention utilizes Cottrell current micro-chronoamperometry in which glucose plus an oxidized electron acceptor produces gluconic acid and a reduced acceptor. This determination involves a preceding chemical oxidation step catalyzed by a bi-substrate bi-product enzymatic mechanism as will become apparent throughout this specification.

In this method of quantification, the measurement of a diffusion controlled current at one or more accurately specified times (e.g., 5, 10, or 15 seconds) after the instant of application of a potential has the applicable equation for amperometry at a controlled potential (E=constant) of:

$$i_{COTTRELL \atop at\ t>0} = (nFA(Dt))^{-0.5} \cdot C_{analyte \atop at\ t=0}$$

which may also be expressed as:

$$i(t) = nFAC_{metabolite}(D)^{0.5}(\pi t)^{-0.5}$$

where i denotes current, nF is the number of coulombs per mole, A is the area of the electrode, D is the diffusion coefficient of the reduced form of the reagent, t is the preset time at which the current is measured, and C is the concentration of the metabolite. Measurements by the method according to the present invention of the current due to the reoxidation of the acceptors were found to be proportional to the glucose concentration in the sample.

The method and apparatus of the present invention permit, in preferred embodiments, direct measurements of blood glucose, cholesterol and the like. Furthermore, the sample cell according to the present invention, provides the testing of controlled volumes of blood without premeasuring. Insertion of the sample cell into the apparatus thus permits automatic functioning and timing of the reaction allowing for patient self-testing with a very high degree of precision and accuracy.

One of many of the presently preferred embodiments of the invention for use in measuring B-D glucose is described in detail to better understand the nature and scope of the invention. In particular, the method and apparatus according to this embodiment are designed to provide clinical self-monitoring of blood glucose levels by a diabetic patient. The sample cell of the invention is used to control the sampling volume and reaction media and acts as the electrochemical sensor. In this described embodiment, benzoquinone is used as the electron acceptor.

The basic chemical binary reaction utilized by the method according to one preferred embodiment of the present invention is:

B-D-glucose+Benzoquinone+$H_2O$→Gluconic Acid→Hydroquinone Hydroquinone→benzoquinone−2e−+2H+.

The first reaction is an oxidation reaction which proceeds to completion in the presence of the enzyme glucose oxidase. Electrochemical oxidation takes place in the second part of the reaction and provides the means for quantifying the amount of hydroquinone produced in the oxidation reaction. This holds true whether catalytic oxidation is conducted with two-electron acceptors or one electron acceptor such as ferricyanide [wherein the redox couple would be $Fe(CN)_6^{-3}/Fe(CN)_6^{-4}$], ferricinium, cobalt III orthophenanthroline and cobalt (III) dipyridyl.

Catalytic oxidation by glucose oxidase is highly specific for B-D-glucose, but is nonselective as to the oxidant. It has now been discovered that the preferred oxidants described above have sufficiently positive potentials to convert substantially all of the B-D-glucose to gluconic acid. Furthermore, this system provides a means by which amounts as small as 1 mg of glucose (in the preferred embodiment) to 1000 mg of glucose can be measured per deciliter of sample—results which have not previously been obtained using other glucose self-testing systems.

The sensors containing the chemistry to perform the desired determination, constructed in accordance with the present invention, are used with a portable meter for self-testing systems. In use, the sensor is inserted into the meter, which turns the meter on and initiates a wait for the application of the sample. The meter recognizes sample application by the sudden charging current flow that occurs when the electrodes and the overlaying reagent layer are initially wetted by the sample fluid. Once the sample application is detected, the meter begins the reaction incubation step (the length of which is chemistry dependent) to allow the enzymatic reaction to reach completion. This period is on the order of 15 to 90 seconds for glucose, with incubation times of 20 to 45 seconds preferred. Following the incubation period, the instrument then imposes a known potential across the electrodes and measures the resulting diffusion limited (i.e., Cottrell) current at specific time points during the Cottrell current decay. Current measurements can be made in the range of 2 to 30 seconds following potential application with measurement times of 10 to 20 seconds preferred. These current values are then used to calculate the analyte concentration which is then displayed. The meter will then wait for either the user to remove the sensor or for a predetermined period before shutting itself down.

Figure 11:
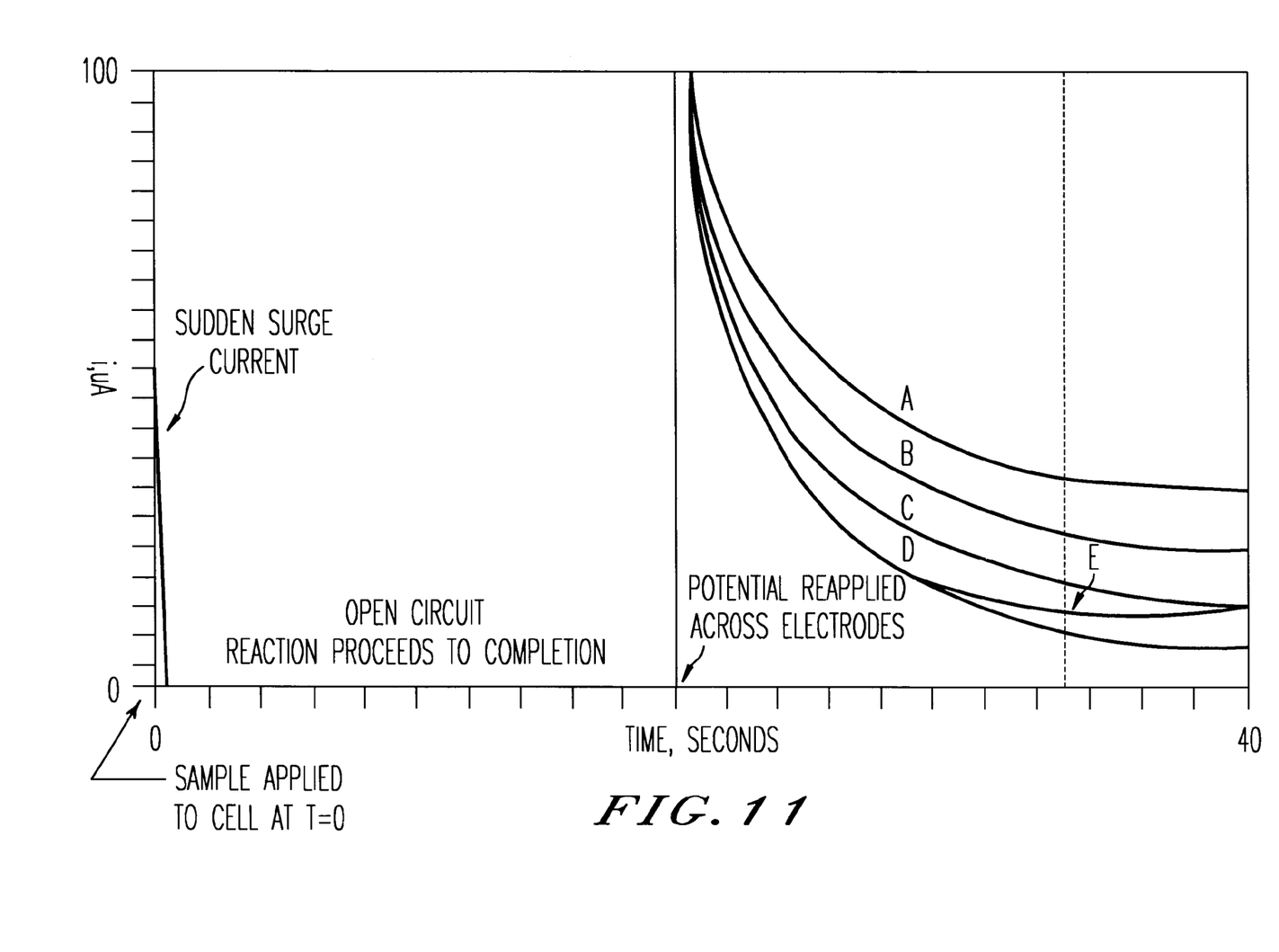
FIG. 11 is a graph showing multiple current measurements of the present invention.
Figure 12:
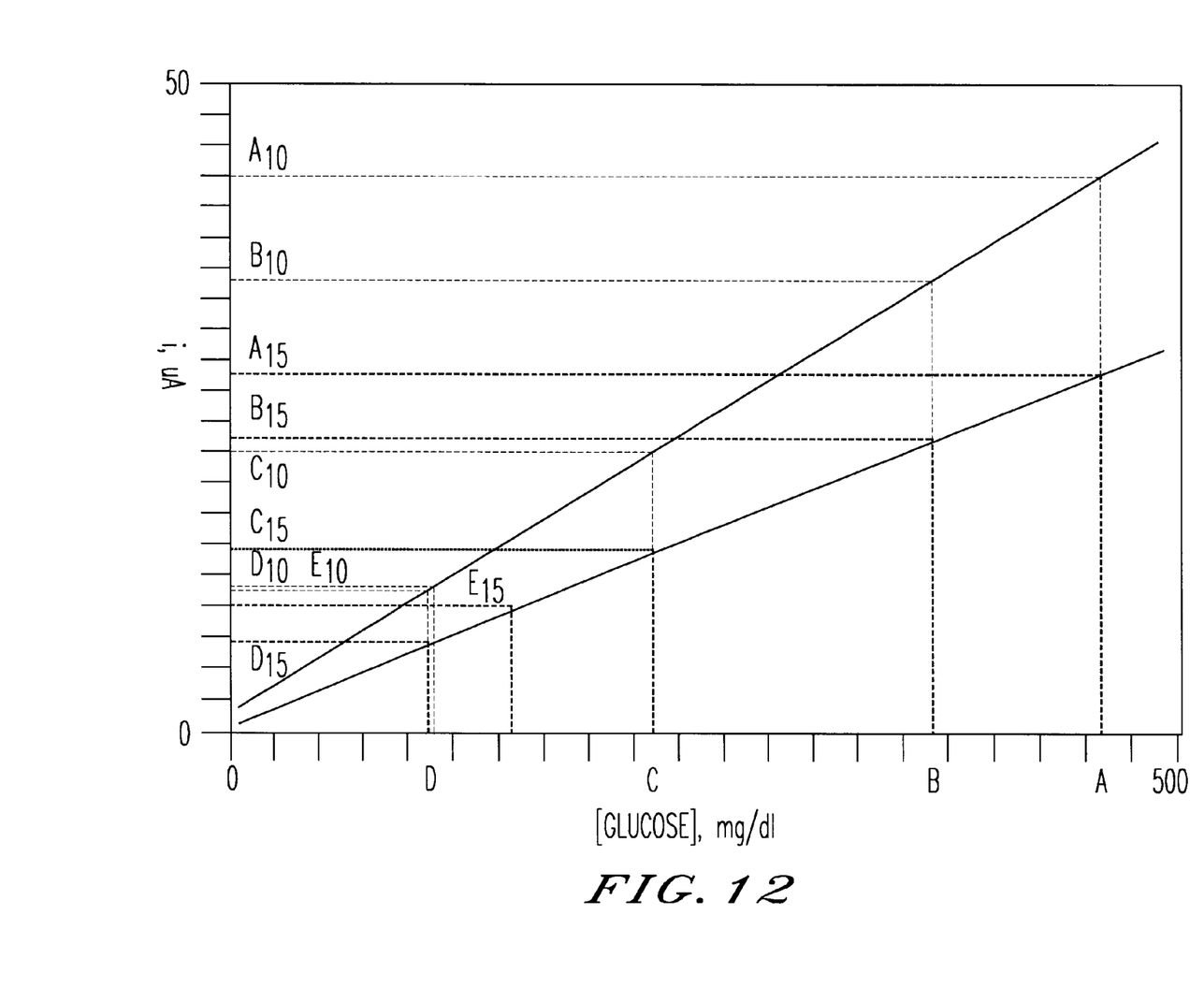
FIG. 12 is a graph correlating measured current to glucose concentration for the curves of FIG. 11.
Figure 13:
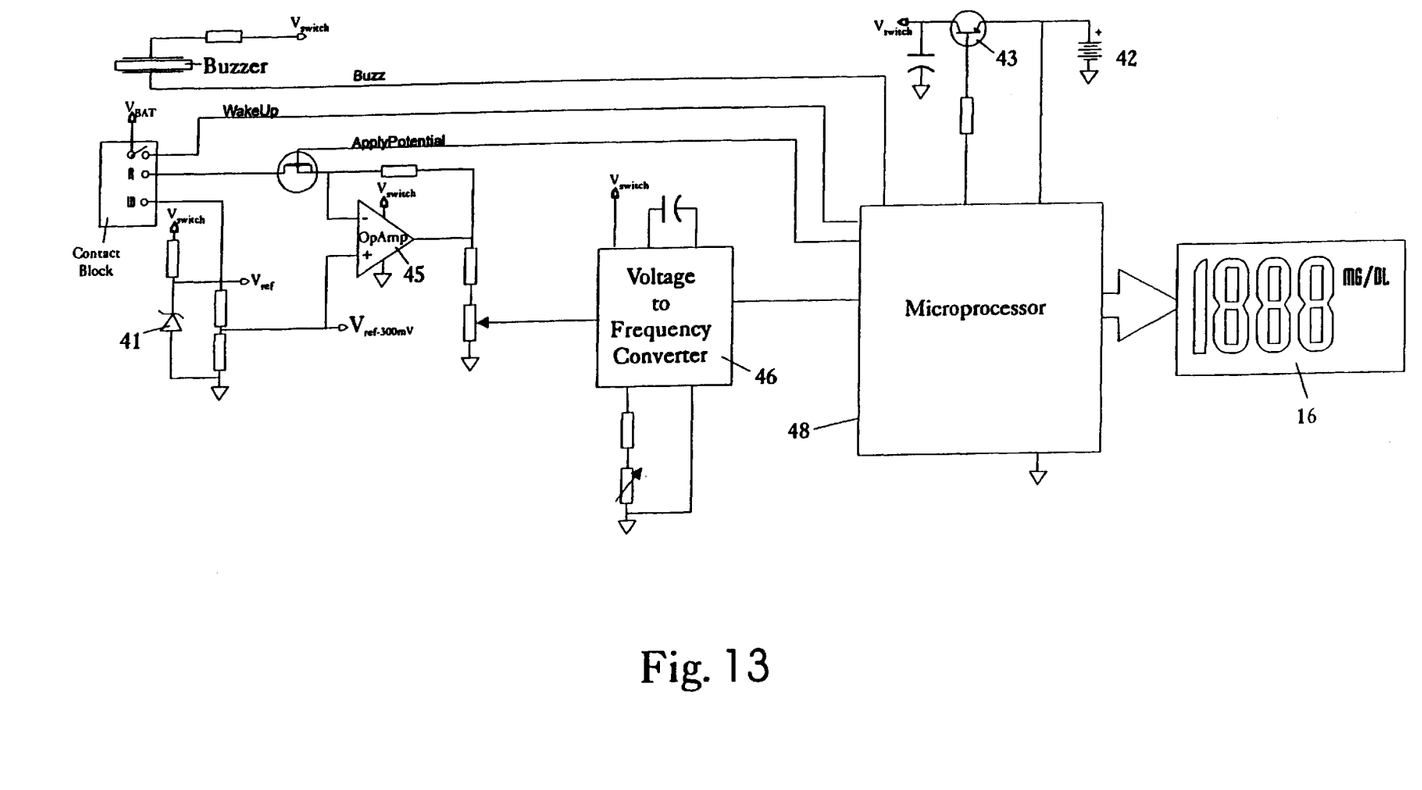
FIG. 13 is a schematic circuit diagram depicting a preferred embodiment of the invention.

Due to the nature of the Cottrell current, it is possible to develop a calibration curve at more than one time point following application of the potential in order to verify that the measurement is being accurately made. Results can then be calculated at the different time points and compared. This is illustrated schematically in FIGS. 11 and 12; which indicate expected, or "normal" Cottrell curves, A, B, C, D, for various glucose concentrations and an abnormal curve E, showing divergence from expected curve D as indicated by the multiple current readings. In a system that is operating correctly, the results should agree within reasonable limits. The exact range of acceptable difference between the expected and measured currents depends on a number of compromises but would generally be in the range of 1–10%. Results outside of the acceptable limits would indicate some problem with the system. For instance, incomplete wetting of the reagent (i.e., too small of a drop of blood) would result in failure to follow the Cottrell curve decay and result in a higher value being calculated at subsequent measurement points than would have been expected for Cottrell current curve delay. FIG. 13 represents a schematic circuit diagram which can be employed in producing a preferred embodiment of the invention for taking multiple current measurements.

The present invention provides for a measurement system that eliminates several of the critical operator dependant variables that adversely affect the accuracy and reliability and provides for a greater dynamic range than other self-testing systems.

These and other advantages of the present invention will become apparent from a perusal of the following detailed description of one embodiment presently preferred for measuring glucose and other analytes which is to be taken in conjunction with the accompanying drawings in which like numerals indicate like components and in which:

Figure 1:
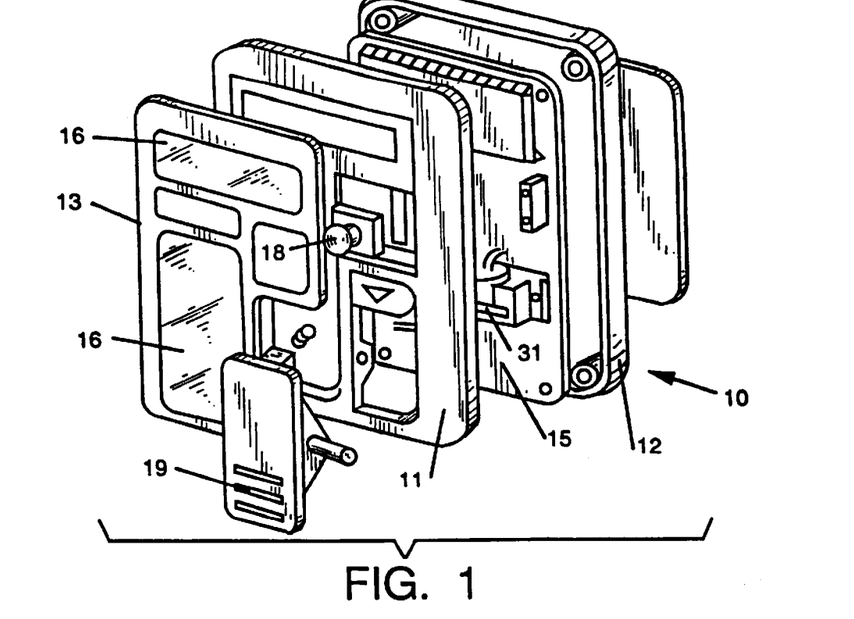
FIG. 1 is an exploded view of a portable testing apparatus according to the present invention.

With specific reference to FIG. 1, a portable electrochemical testing apparatus 10 is shown for use in patient self-testing, such as, for example, for blood glucose levels. Apparatus 10 comprises a front and back housing 11 and 12, respectively, a front panel 13 and a circuit board 15. Front panel 13 includes graphic display panels 16 for providing information and instructions to the patient, and direct read-out of the test results. While a start button 18 is provided to initiate an analysis, it is preferred that the system begin operation when a sample cell 20 (FIG. 2) is inserted into the window 19 of the apparatus.

Figure 2:
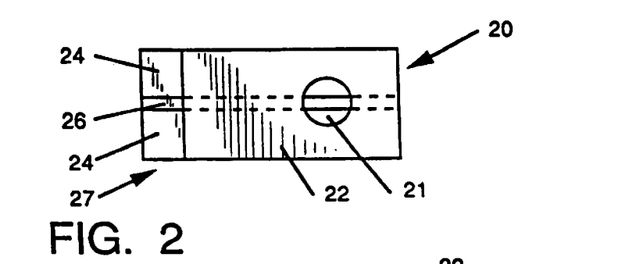
FIG. 2 is a plan view of the sampling cell of the present invention.
Figure 3:
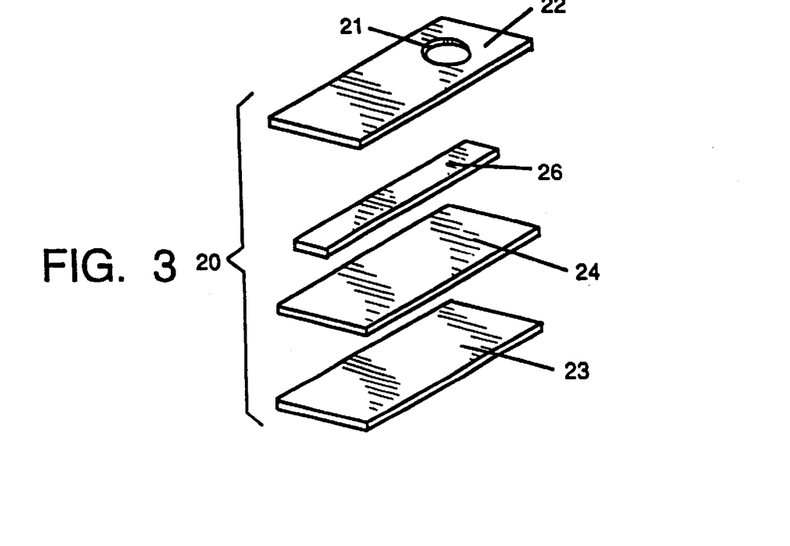
FIG. 3 is an exploded view of the sample cell shown in FIG. 2.

With reference to FIGS. 2 and 3, sample cell 20 is a metallized plastic substrate having a specifically-sized opening 21 which defines a volumetric well 21, when the cell is assembled, for containing a reagent pad and the blood to be analyzed. Cell 20 comprises a first substrate 22 and a second substrate 23 which may be preferably made from styrene or other substantially non-conducting plastic, such as polyimide, polyethylene, etc. Polyimide has proven particularly preferred because the metal adheres well to it, and the electrodes may be more readily slitted to the desired width. Polyimide sold under the trademark KAPTON, and available from DuPont, has proven particularly advantageous.

Positioned on second substrate 23 is reference electrode 24. Reference electrode 24 may be preferably manufactured, for example, by vapor depositing or "sputtering" the electrode onto a substrate made from a material such as the polyimide Kapton. In one preferred embodiment, reference electrode 24 is a silver—silver chloride electrode. This electrode can be produced by first depositing a silver chloride layer on a silver layer by either chemical or electrochemical means before the substrate is used to construct the cells. The silver chloride layer may even be generated in-situ on a silver electrode when the reagent layer contains certain of the oxidants, such as ferricyanide, and chloride as shown in the following reactions:

Alternatively the silver—silver chloride electrode can be produced by depositing a layer of silver oxide (by reactive sputtering) onto the silver film. The silver oxide layer is then converted in-situ at the time of testing to silver chloride according to the reaction:

when the sensor is wetted by the sample fluid and reconstitutes the chloride containing reagent layer. The silver electrode is thus coated with a layer containing silver chloride.

The reference electrode may also be of the type generally known as a "pseudo" reference electrode which relies upon the large excess of the oxidizing species to establish a known potential at a noble metal electrode. In a preferred embodiment, two electrodes of the same noble metal or carbon are used, however one is generally of greater surface area and is used as the reference electrode. The large excess of the oxidized species and the larger surface area of the reference resists a shift of the potential of the reference electrode.

The primary requirement for the pseudo-reference (as is also the case with traditional reference electrodes) is that it should be able to supply the necessary current (in opposition to the current flow at the working electrode) without significant shift in its potential. Providing a larger surface area for the reference electrode than for the working electrode is one way to accomplish this. When high concentration of the oxidant are utilized and/or the range of currents is kept relatively low, e.g., less than about 20 to 40 milliamps/cm$^2$, with 0.1M ferricyanide as the oxidant, it is possible to reduce the ratio of the reference to working electrode to 1:1 or even less. The use of equal size electrodes offers some advantage in terms of manufacture but with potentially a limitation to the upper range.

In the case of same size (i.e., same surface area) electrodes, a large excess of oxidized species (i.e., wherein the oxidized form of the redox mediator (i.e., ferricyanide) is present in the reagent layer in sufficient excess to insure that the diffusion limited electrooxidation of the redox mediator at the working electrode surface is the principal limiter of current flow through the cell and resists a shift of the potential of the second electrode (i.e., pseudo-reference) vis-a-vis the first (i.e., working) electrode.

In a highly preferred embodiment of the invention, the two-electrode system uses same size, same metal electrodes. Preferably noble metals, such as palladium are used. In this palladium vs. palladium embodiment, a potential of +0.30 volts applied between the electrodes has proven effective when ferricyanide is the oxidant. Acceptable same-size palladium vs. palladium coplanar-electrodes may be produced from metalized plastic slitted by a high performance slitter such as Metlon Corp., 133 Francis Avenue, Cranston, R.I. 02910.

In the pseudo-reference instance, care must be exercised in the spacing of the electrodes. This is due to the fact that as the second electrode functions to provide the balancing current, it is actually producing the reduced form of the oxidant (redox mediator). If the electrodes are spaced too closely together, the reduced form produced at the second electrode can diffuse toward the working electrode, where it would then be re-oxidized, adding to the current flow due to the oxidation of the reduced form produced by the enzymatic reaction. The net effect would be a departure from the expected Cottrell current decay curve illustrated in FIGS. 7 and 11.

This problem is potentially aggravated when the size of the second electrode, vis-a-vis the first, is reduced, such as in the case of same-size electrodes or when the second electrode is smaller than the working electrode. This is due to the higher effective concentration of reduced oxidant produced over the surface of the second electrode. This can be shown by the following analysis. The current flow at the two electrodes can be represented by the Cottrell equation. For the first electrode, that is:

$$i_t = \frac{nFA_{1st}DC_{1st}}{\sqrt{\pi Dt}}$$

At the second electrode that is:

$$i_t = \frac{nFA_{2nd}DC_{2nd}}{\sqrt{\pi Dt}}$$

Since the two currents must be of the same magnitude (but opposite sign), the following is true at any given time:

$$dC_{1st}A_{1st} = dC_{2nd}A_{2nd}$$

Where $A_{1st}$ is the area of the first (i.e., working) electrode, $C_{1st}$ is the concentration of the reduced form of oxidant in the solution in the reagent layer at time zero (the instant the potential is applied), $A_{2nd}$ is the area of the second (i.e., reference or counter) electrode, and $C_{2nd}$ is the concentration of reduced form of the oxidant generated at or by the second electrode at time zero (the instant the potential is applied).

Since the working electrode is poised to control the current flow, the second electrode acts to balance current flow. Thus, the smaller the second electrode, the higher the concentration of the reduced oxidant produced at the surface of that electrode; the higher the concentration, the greater the diffusion gradient and the greater the potential for the reduced oxidant produced at the second electrode to diffuse towards the working electrode and cause an undesired additional current flow, resulting in a departure from expected Cottrell current flow for the system. First and second electrodes 424, 426 must be spaced apart by a distance d (FIG. 10) sufficient to avoid this departure from expected Cottrell current. A distance d of at least 0.1 mm, preferably greater than 0.1 mm, has proven effective at current flows of 0–50 microamps and about 5 mm² working electrode area. The higher the expected current density, the greater d must be in order to insure true Cottrell measurement. Also, if measurement times exceed about 30 seconds, it is necessary to increase the distance d. In a highly preferred embodiment of the invention, d is about 1–2 mm, $A_{1st}$ and $A_{2nd}$ are both about 5 mm², current flow is about 0–100 microamps, with measurement time of less than 30 seconds.

The maximum spacing for d is dictated by the conductivity of the solution, which effects to the actual voltage at the electrodes (obviated in 3-electrode systems). Practical considerations, however, dictate that the spacing d be as small as technically feasible to minimize substrate, reagent, and sample size requirements. Ideally, the preferred sample is the size of a drop of blood of less than 20 microliters, which must bridge the electrodes and wet the reagent layer. As a practical matter, the spacing d should not exceed about 1 cm because of the difficulty of bridging such a gap with a drop of blood of this size and substantially instantaneously spreading that drop of blood across the reagent layer. It is important that the sample, i.e., blood, spread across the reagent layer substantially instantaneously following application of the sample to the cell, in order to avoid migration of reagents, or erosion of reagents from the site at which the drop of blood was applied. The wicking layer is helpful in this regard.

EXAMPLE 1

A two mm² palladium indicator electrode was referenced to a two mm² Ag/Ag$_2$O electrode and the electrodes were spaced apart by a 2 mm gap. Measurements were taken from sample cells including the reagents described herein, including an analyte (i.e., glucose) the oxidized form of a redox mediator (i.e., ferricyanide), an enzyme (i.e., glucose oxidase), and a buffer (i.e., phosphate). Preferably, in the case of same size, same noble metal electrodes, the oxidized form of the redox mediator is present in sufficient quantity to insure that the counter electrode current, i.e., that produced at the reference electrode, is not limiting as a result of conversion to the reduced form of the redox mediator at the working electrode surface. The data for the results, summarized in Table 1, were obtained 10 seconds after current was applied.

For 5 millimolar ferrocyanide corresponding to 4 millimolar glucose (72 mg/dl), an average current of 27.1 microamps was obtained. The relative standard deviation was 5.3%. For 20 millimolar ferrocyanide, an average current of 102.9 was obtained and the relative standard deviation was 3.9%. In this experiment, the volumes tested were 50 microliters, although smaller volumes such as 10 microliters could be employed if the area of the 2 mm² electrode strips were decreased.

A concentration series for ferrocyanide from 0 through 30 millimolar was similarly obtained. A plot of the currents at 10 seconds vs. ferrocyanide concentration indicated a linearly increasing current with concentration through 25 millimolar (approximately 360 mg/dl glucose). Similar results can be obtained when both same-size electrodes are the same noble metal, such as palladium.

The buffer used in the reagent layer is preferably non-reactive with respect to the reduced and oxidized form of the redox mediator (i.e., has a higher oxidation potential). Phosphate buffer has proven effective in this regard, although other suitable buffers would, of course, now be readily apparent to those of ordinary skill in the art.

| Cottrell Current, microamps, at 10 seconds after E is applied | Fe $(CN)_6^{4-}$ Concentration millimolar | Corresponding Glucose Concentration, mg/dl |
|---|---|---|
| 0 | 0 | 0 |
| 27 | 5 | 72 |
| 58 | 10 | 144 |
| 75 | 15 | 216 |
| 103 | 20 | 288 |
| 142 | 25 | 360 |
| 136 | 30 | 432 |

Figure 10:
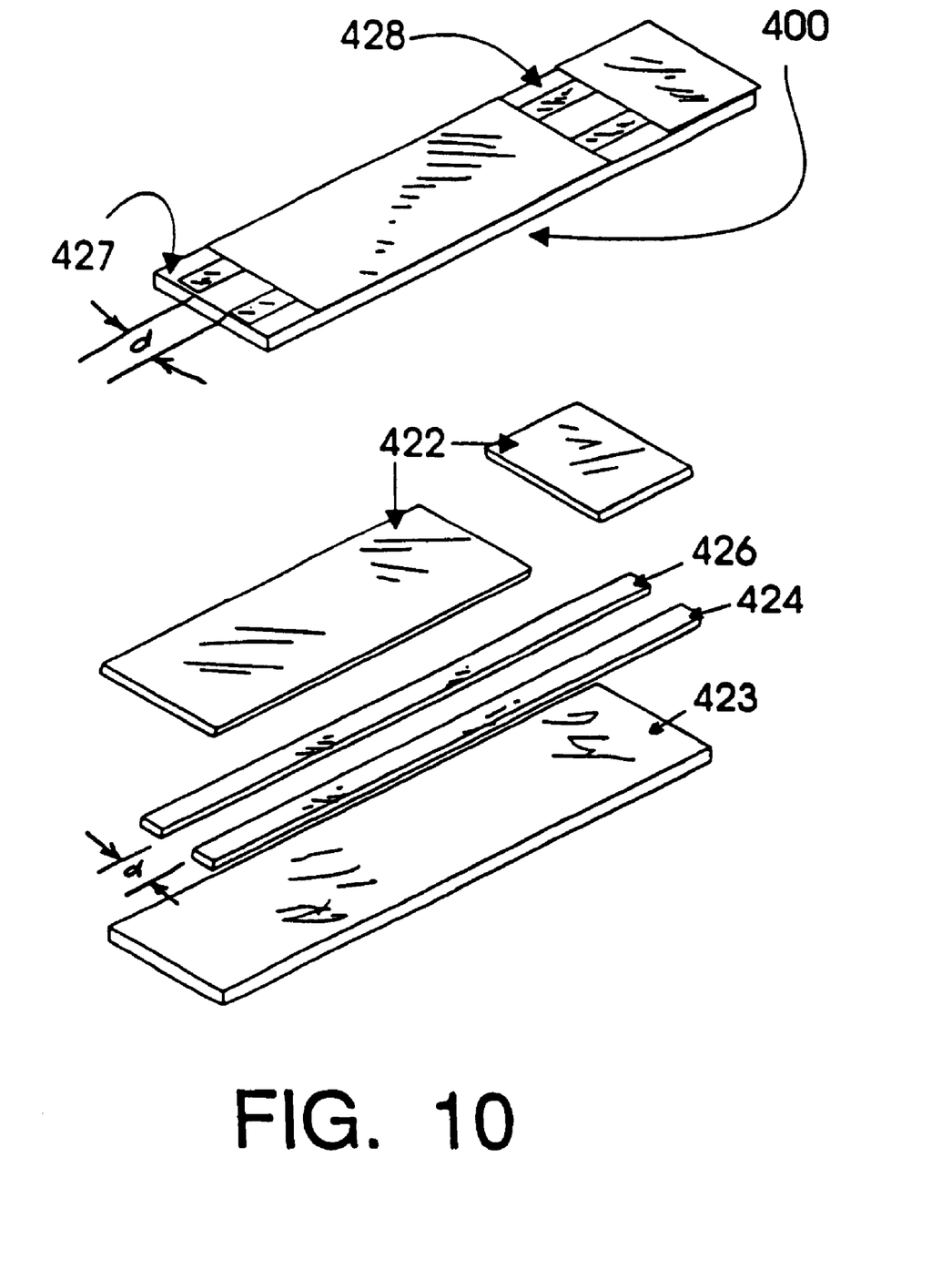
FIG. 10 is a preferred embodiment of the invention wherein the two electrodes are co-planar, equal size, and preferably the same noble metal.

Indicator or working electrode 26 can be either a strip of platinum, gold, or palladium positioned on reference electrode 24, or, alternately, as shownned in FIG. 10, the working electrodes426 and reference electrode 424 are laminated between an upper 422 and lower 423 non-conducting (i.e. electrically insulating) material, such as polyethylene or polystyrene. Preferably, sample cell 20 is prepared by sandwiching or laminating the electrodes between the substrate to form a composite unit. Of course, other methods of applying the metal or other electrically conducting material, such as, without limitation, silk screening, vapor deposition, electrolysis, adhesion, etc., may also be employed.

Of course, any combination of suitable electrode pairs may be used. Names other than "working" vs. "reference" electrodes which have been interchangeably used in electrochemical applications include, "working" v.s. "counter" electrodes, "excitation" v. "source" electrodes, or three electrode systems having a "working" electrode, a "reference" electrode, and an "auxiliary" electrode. In the case of a three-electrode system, the auxiliary electrode completes the circuit, allowing current to flow through the cell, while the reference electrode maintains a constant interfacial potential difference regardless of the current. In the two electrode scenario, the second electrode serves both the function of an auxiliary and reference electrode. Regardless of the nomenclature employed, the electrochemistry of interest in the present invention occurs at a first electrode (i.e., working) and a second electrode (i.e., reference or counter) acts to counter balance current flow (i.e., provide opposing current flow to the first electrode) and fix the operating potential of the system.

As shown in FIG. 2, first substrate 22 is of a slightly shorter length so as to expose an end portion 27 of electrodes 24 and 26 and allow for electrical contact with the testing circuit contained in the apparatus. In this embodiment, after a sample has been positioned within well 21, cell 20 is pushed into window 19 of the front panel to initiate testing. In this embodiment, a reagent may be applied to well 21, or, preferably, a pad of dry reagent is positioned therein and a sample (drop) of blood is placed into the well 21 containing the reagent.

Figure 4:
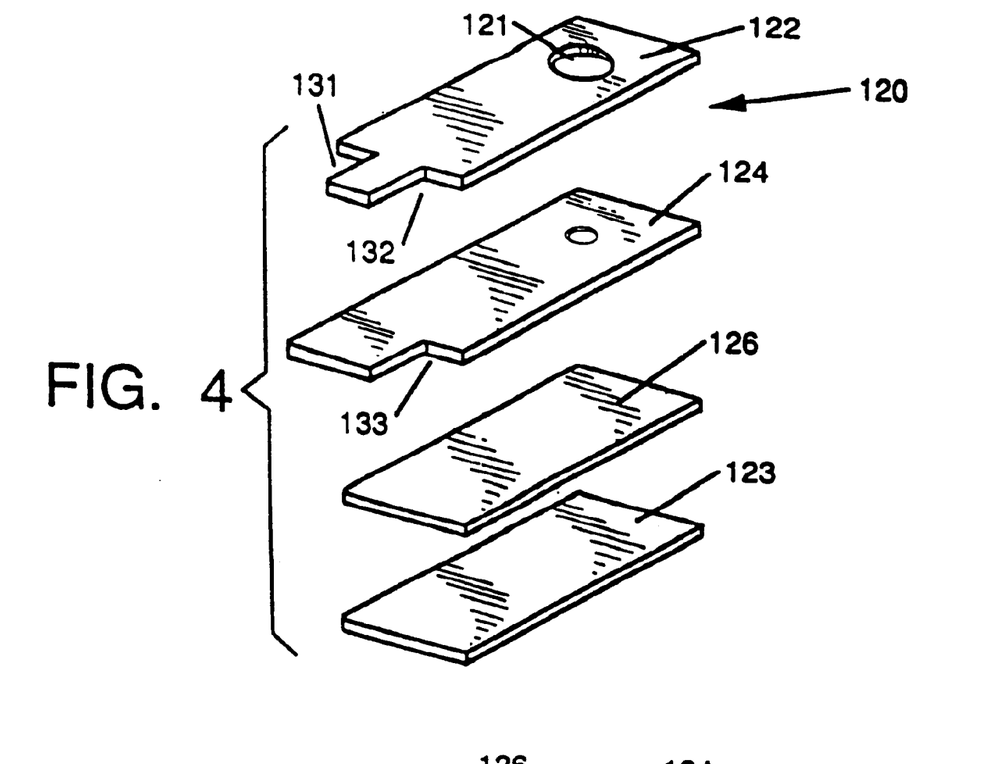
FIG. 4 is an exploded view of another embodiment of a sample cell according to the invention.
Figure 5:
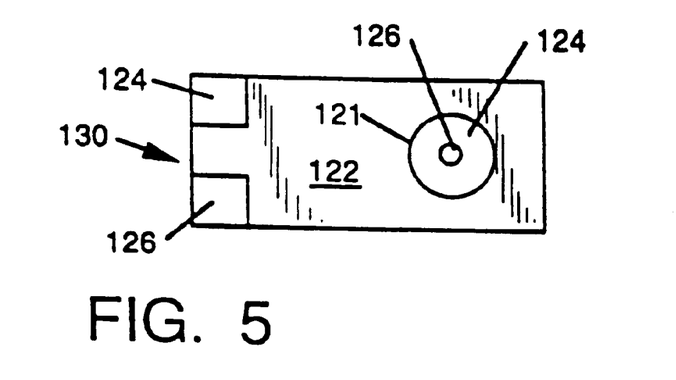
FIG. 5 is a plan view of the cell shown in FIG. 4.

Referring to FIGS. 4–5, alternative embodiments of sample cell 20 are shown. In FIG. 4, sample cell 120 is shown having first 122 and second 123 substrates. Reference electrode 124 and working electrode 126 are laminated between substrates 122 and 123. Opening 121 is dimensioned to contain the sample for testing. End 130 (FIG. 5) is designed to be inserted into the apparatus, and electrical contact is made with the respective electrodes through cut-outs 131 and 132 on the cell. Reference electrode 124 also includes cut out 133 to permit electrical contact with working electrode 126.

Referring to FIGS. 1 and 2, the sample cell according to the present invention is positioned through window 19 (FIG. 1) to initiate the testing procedure. Once inserted, a potential is applied at portion 27 (FIG. 2) of the sample cell across electrodes 24 and 26 to detect the presence of the sample. Once the sample's presence is detected, the potential is removed and the incubation period initiated. Optionally during this period, a vibrator means 31 (FIG. 1) may be activated to provide agitation of the reagents in order to enhance dissolution (an incubation period of 20 to 45 seconds is conveniently used for the determination of glucose and no vibration is normally required). An electrical potential is next applied at portion 27 of the sample cell to electrodes 24 and 26 and the current through the sample is measured and displayed on display 16.

To fully take advantage of the above apparatus, the needed chemistry for the self testing systems is incorporated into a dry reagent layer that is positioned onto the disposable cell creating a complete sensor for the intended analyte. The disposable electrochemical cell is constructed by the lamination of metallized plastics and nonconducting materials in such a way that there is a precisely defined working electrode area. The reagent layer is either directly coated onto the cell or preferably incorporated (coated) into a supporting matrix such as filter paper, membrane filter, woven fabric or non-woven fabric, which is then placed into the cell, substantially covering the electrode surfaces exposed by the cutout portion or window of the electrically insulating upper laminate. When a supporting matrix is used, its pore size and void volume can be adjusted to provide the desired precision and mechanical support. In general, membrane filters or nonwoven fabrics provide the best materials for the reagent layer support. Pore sizes of 0.45 to 50 um and void volumes of 50–90% are appropriate. The coating formulation generally includes a binder such as gelatin, carrageenan, methylcellulose, polyvinyl alcohol, polyvinylpyrrolidone, etc., that acts to delay the dissolution of the reagents until the reagent layer has absorbed most of the fluid from the sample. The concentration of the binder is generally on the order of 0.1 to 10% with 1–4% preferred.

The reagent layer imbibes a fixed amount of the sample fluid when it is applied to the surface of the layer thus eliminating any need for premeasurement of sample volume. Furthermore, by virtue of measuring current flow rather than reflected light, there is no need to remove the blood from the surface of the reagent layer prior to measurement as there is with reflectance spectroscopy systems. While the fluid sample could be applied directly to the surface of the reagent layer, to facilitate spread of blood across the entire surface of the reagent layer the sensor preferably includes a dispersing spreading or wicking layer. This layer, generally a nonwoven fabric or adsorbent paper, is positioned over the reagent layer and acts to rapidly distribute the blood over the reagent layer. In some applications this dispersing layer could incorporate additional reagents.

For glucose determination, cells utilizing the coplanar design were constructed having the reagent layer containing the following formulations: I

| | |
|---|---|
| Glucose oxidase | 600 units/ml |
| Potassium Ferricyanide | 0.4M |
| Phosphate Buffer | 0.1M |
| Potassium Chloride | 0.5M |
| Gelatin | 2.0 g/dl |

This was produced by coating a membrane filter with a solution of the above composition and air drying. The reagent layer was then cut into strips that just fit the window opening of the cells and these strips were placed over the electrodes exposed within the windows. A wicking layer of a non-woven rayon fabric was then placed over this reagent layer and held in place with an overlay tape.

As will now be readily appreciated by those of ordinary skill in the art, the enzyme (i.e., glucose oxidase) is sufficient in type and amount to catalyze the reaction (i.e., receive at least one electron from the reaction) involving the enzyme, the analyte (i.e., glucose) and the oxidized form of the redox mediator (i.e., ferricyanide). Optionally, surfactant can also be used in the reagent layer to promote wetting of the reagent by the sample containing the analyte.

In order to prove the application of the technology according to the present invention, a large number of examples were run in aqueous solution at 25° C. The electrolyte consisted of a phosphate buffer of pH 6.8 which was about 0.1 molar total phosphate and 0.5M potassium chloride reagent. The potentials are referenced to a normal hydrogen electrode (NHE). In these tests it was found that any potential between approximately +0.8 and 1.2 volt (vs NHE) is suitable for the quantification of hydroquinone when benzoquinone is used as the oxidant. The limiting currents are proportional to hydroquinone concentrations in the range between 0.0001M and 0.050M.

Determination of glucose by Cottrell current ($i_t$) microchronoamperometry with the present method is created in the reaction of hydroquinone to benzoquinone. Cottrell currents decay with time in accordance with the equation:

$$i_t t^{1/2} = \text{const}$$

where t denotes time.

Figure 6:
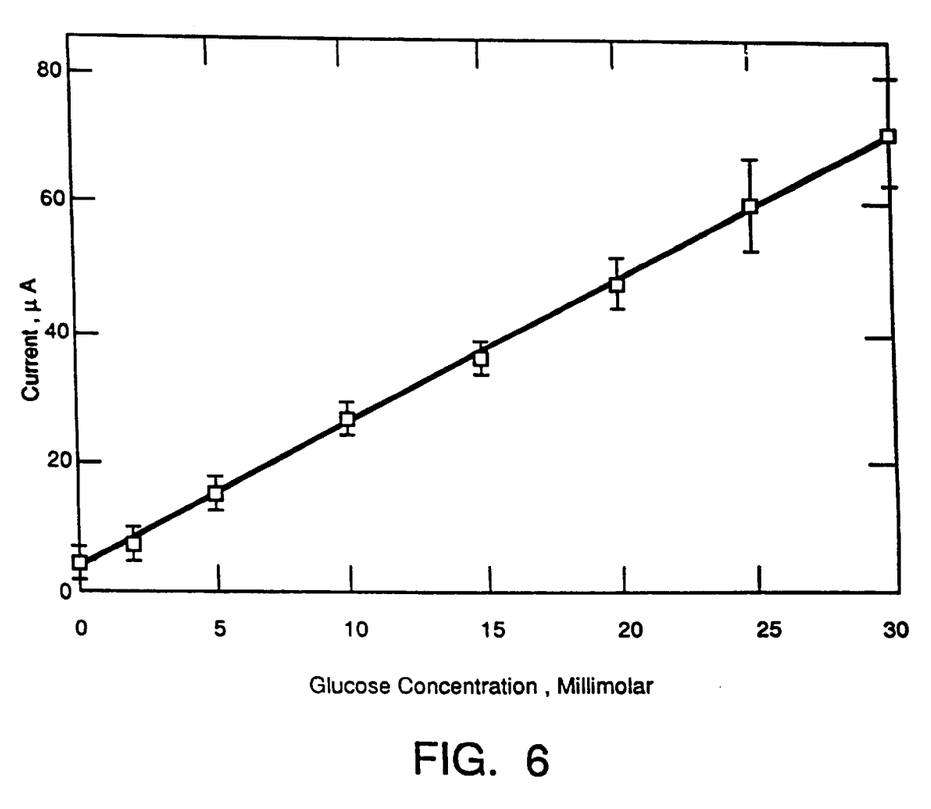
FIG. 6 is a graph showing current as a function of glucose concentration.
Figure 7:
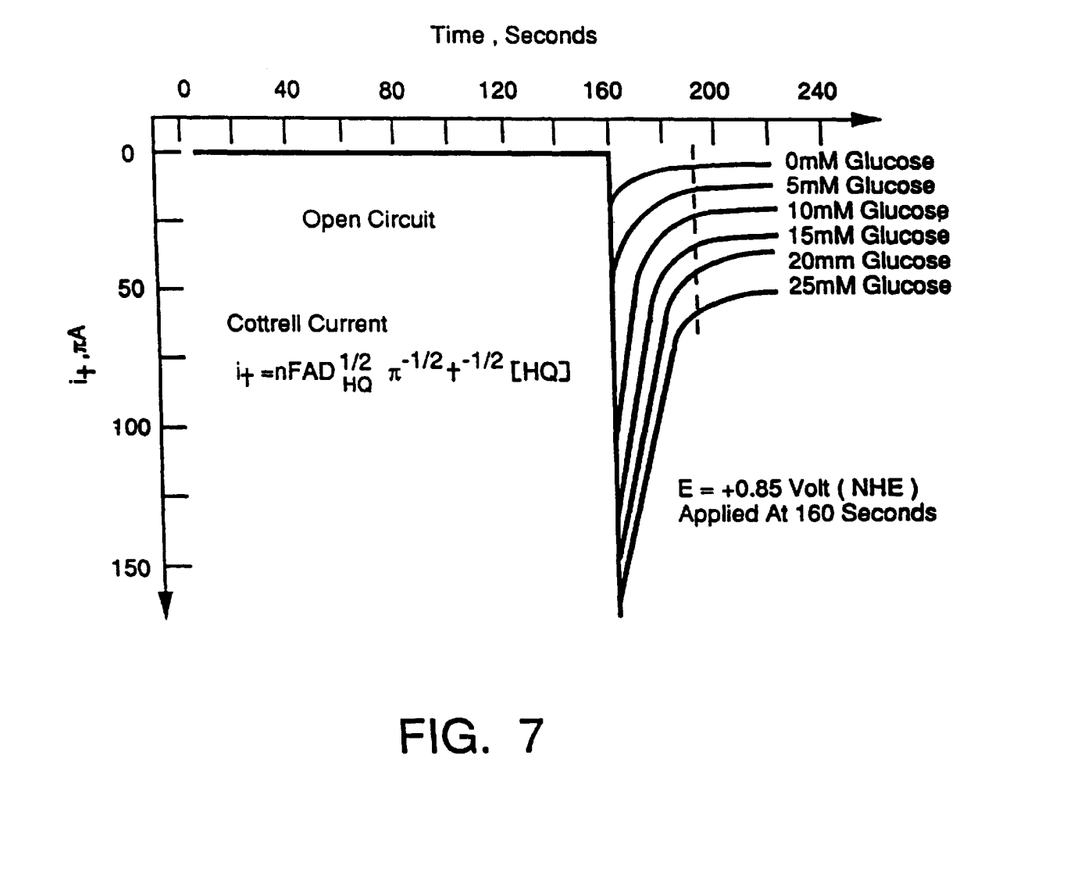
FIG. 7 is a graphical presentation of Cottrell current as a function of glucose concentration.

The main difference between these two techniques consists of applying the appropriate controlled potential after the glucose-benzoquinone reaction is complete and correlating glucose concentrations with Cottrell currents measured at a fixed time thereafter. The current-time readout is shown in FIG. 7. Proportionality between glucose concentrations and Cottrell currents (recorded at t=30 seconds after the application of potential) is shown in FIG. 6.

It should be noted that Cottrell chronoamperometry of metabolites needs the dual safeguards of enzymatic catalysis and controlled potential electrolysis. Gluconic acid yields of 99.9+ percent were attained in the presence of glucose oxidase. Concomitantly, equivalent amounts of benzoquinone were reduced to hydroquinone, which was conveniently quantitated in quiescent solutions, at stationary palladium thin film anodes or sample cells.

The results of these many tests demonstrates the microchronoamperometric methodology of the present invention and its practicality for glucose self-monitoring by diabetics.

In a presently preferred embodiment of the invention utilizing ferricyanide, a number of tests were run showing certain improved operating capabilities.

Figure 8:
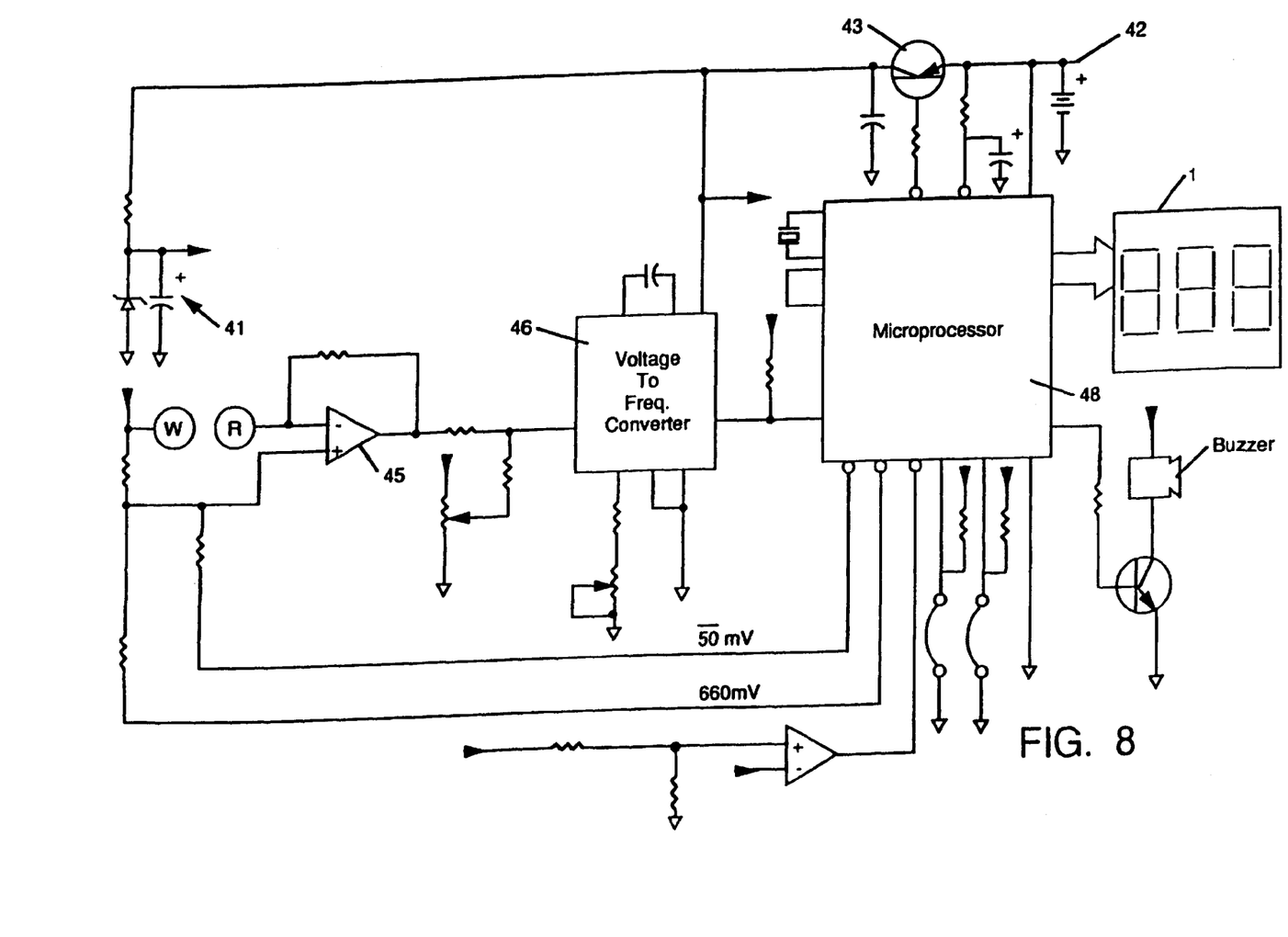
FIG. 8 is a presently preferred circuit diagram of an electrical circuit for use in the apparatus shown in FIG. 1.

Referring to FIG. 8, a schematic diagram of a preferred circuit 15 for use in the apparatus 10 is shown. Circuit 15 includes a microprocessor and LCD panel 16. The working and reference electrodes on the sample cell 20 make contact at contacts W (working electrode) and R (reference electrode), respectively. Voltage reference 41 is connected to battery 42 through analogue power switch 43. Current from electrodes W and R is converted to a voltage by op amp 45. That voltage is converted into a digital signal (frequency) by a voltage to frequency converter 46 electrically connected to the microprocessor 48. The microprocessor 48 controls the timing of the signals. Measurement of current flow is converted by microprocessor 48 to equivalent glucose, cholesterol or other substance concentrations. Other circuits within the skills of a practiced engineer can now be utilized to obtain the advantages of the present invention.

Figure 9:
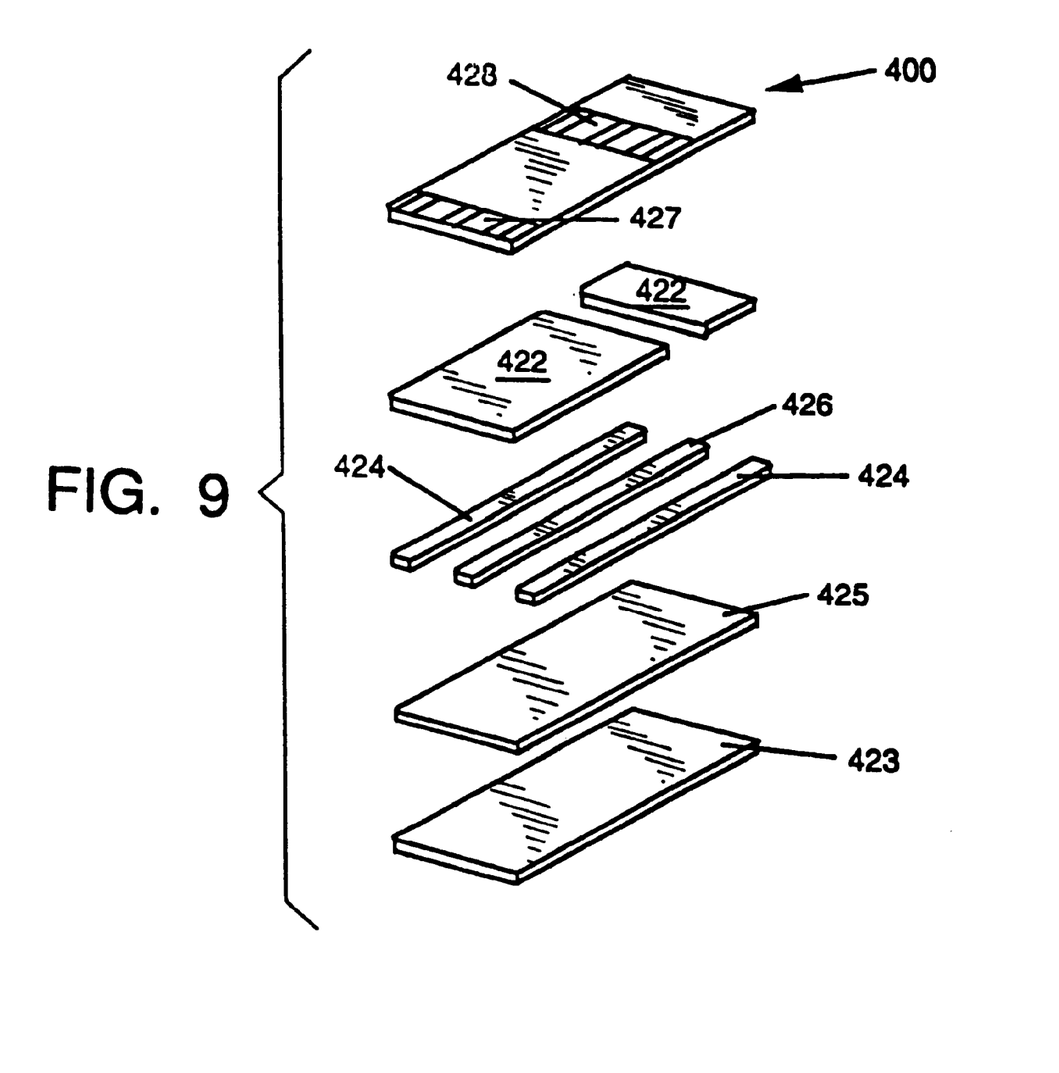
FIG. 9 is a preferred embodiment of the electrochemical cell of the invention wherein the reference electrode area is greater than the working electrode area.

With regard to FIG. 9, cell 400 consists of coplanar first (i.e., working) 426 and second (i.e., reference) 424 electrodes laminated between an upper 422 and lower 423 nonconducting (i.e., electrically insulating) material. Lamination is on an adhesive layer 425. The upper material 422 includes a die cut opening 428 which, along with the width of the working electrode material defines the working electrode area and provides (with an overlapping reagent layer not depicted) the sampling port of the cell. As illustrated, this die-cut opening is rectangular or square, which has proven advantageous from the standpoint of reproduceability, as such openings are more readily centered over the co-planar electrodes than circular openings. At one end of cell 400 is an open area 427 similar to end position 27 of FIG. 2. In the case of same size (i.e., same surface area first and second electrodes 426, 424 as illustrated in FIG. 10), the opening 428 insures that equal surface areas of the first and second electrodes are exposed.

The efficiency of using the apparatus according to the present invention to provide a means for in home self testing by patients such as diabetics (in the preferred embodiment) can be seen in the following table in which the technology according to the present invention is compared to four commercially available units. As will be seen, the present invention is simpler, and in this instance simplicity breeds consistency in results.

| GLUCOSE SYSTEM COMPARISONS | | | | | |
|---|---|---|---|---|---|
| Steps | 1 | 2 | 3 | 4 | Present Invention |
| Turn Instrument On | X | X | X | X | X |
| Calibrate Instrument | X | X | | | |
| Finger Puncture | X | X | X | X | X |
| Apply Blood | X | X | X | X | X |
| Initiate Timing | X | X | X | | |
| Sequence Blot | X | X | X | | |
| Insert Strip to Read | X | X | X | X | |
| Read Results | X | X | X | X | X |
| Total Steps Per Testing | 8 | 8 | 7 | 5 | 4 |
| Detection System | RS' | RS | RS | RS | Polarographic |
| Range (mg/dl) CV" | 10–400 | 40–400 | 25–450 | 40–400 | 0–1000 |
| Hypoglycemic | 15% | 15% | | | 5% |
| Euglycemic | 10% | 10% | | | 3% |
| Hyperglycermic | 5% | 5% | | | 2% |
| Correlation | 0.921 | 0.862 | | | 0.95 |

'RS - Reflectance Spectroscopy
"Coefficient of variation

Thus, while we have illustrated and described the preferred embodiment of our invention, it is to be understood that this invention is capable of variation and modification, and we therefore do not wish or intend to be limited to the precise terms set forth, but desire and intend to avail ourselves of such changes and alterations which may be made for adapting the present invention to various usages and conditions. Accordingly, such changes and alterations are properly intended to be within the full range of equivalents, and therefore within the purview, of the following claims. The terms and expressions which have been employed in the foregoing specifications are used therein as terms of description and not of limitation, and thus there is no intention, in the use of such terms and expressions, of excluding equivalents of the features shown and described or portions thereof, it being recognized that the scope of the invention is defined and limited only by the claims which follow.

Having thus described our invention and the manner and process of making and using it in such full, clear, concise, and exact terms so as to enable any person skilled in the art to which it pertains, or to with which it is most nearly connected, to make and use the same.

We claim:

1. A method for measuring compounds in a sample fluid in a device including a housing having an access opening therethrough, a sample cell receivable into the access opening of the housing, the sample cell being composed of a first electrode which acts as a working electrode, a second electrode which acts to fix the system potential and provide opposing current flow with respect to the first electrode, the second electrode being made of the same electrically conducting material as the first electrode, and being operatively associated with the first electrode, the ratio of the surface area of the second electrode to the surface area of the first electrode being 1:1 or less, and at least one non-conducting layer member having an opening therethrough, the at least one non-conducting layer member being disposed in contact with at least one of the first and second electrodes and being sealed against at least one of the first and second electrodes to form a known electrode area within the opening such that the opening forms a well to receive the sample fluid and to allow a user of the apparatus to place the sample fluid in the known electrode area in contact with the first electrode and the second electrode, comprising:

a) applying an electrical potential to both the first electrode and said second electrode;
   b) creating an electrical circuit between the first electrode and the second electrode through the sample fluid;
   c) measuring a first Cottrell current reading through the sample fluid at a first predetermined time after the electrical potential is applied and obtaining at least one additional Cottrell current reading through the sample fluid, the at least one additional Cottrell current reading occurring at a second predetermined time following the first predetermined time;
   d) converting the first Cottrell current reading into a first analyte concentration measurement using a calibration slope and an intercept specific for the first Cottrell current measurement, converting the at least one additional Cottrell current reading into an additional analyte concentration using a calibration slope and an intercept specific for the at least one additional Cottrell current measurement, and comparing the first analyte concentration measurement with the at least one additional concentration measurement to confirm that they are within a prescribed percentage of each other; and
   e) visually displaying the results of the analyte concentration measurements.

2. The method of claim 1, further comprising:
   initiating an electrical potential upon insertion of the sample fluid to detect the presence of the sample fluid, signaling to commence a reaction timing sequence when the presence of the sample fluid is detected, and removing the potential during the reaction timing sequence.

3. The method of claim 1, wherein the first and second electrodes are spaced apart by a distance of at least about 0.1 mm and at most about 1 cm.

4. A method for obtaining measurements of an analyte contained in a sample in order to determine the concentration of analyte in the sample, in a device including a first electrical insulator, a pair of electrodes including working and counter electrodes, the working and counter electrodes being made of the same electrically conducting materials and being supported on the first electrical insulator, a second electrical insulator, overlaying the first electrical insulator and the working and counter electrodes and including a cutout portion that exposes surface areas of the working and counter electrodes, a reagent, substantially covering the exposed electrode surfaces in the cutout portion and including the oxidized form of a redox mediator, and an enzyme, the oxidized form of the redox mediator being capable of receiving at least one electron from a reaction involving enzyme, analyte, and the oxidized form of the redox mediator and being in sufficient amount to insure that current produced by diffusion limited electrooxidation as a result of the reaction is limited by the oxidation of the reduced form of the redox mediator at the working electrode surface, the enzyme being present in sufficient amount to catalyze the reaction involving the enzyme, analyte, and the oxidized form of the redox mediator, comprising:

(a) measuring a first Cottrell current attributable to the diffusion limited electrooxidation at a first predetermined time;
   (b) measuring at least one second Cottrell current attributable to the diffusion limited electrooxidation at one or more subsequent predetermined times;
   (c) converting the first Cottrell current into a first analyte concentration measurement using a calibration slope and an intercept specific for the first Cottrell current measurement;
   (d) converting the at least one second Cottrell current reading into an additional analyte concentration using a calibration slope and an intercept specific for the at least one second Cottrell current measurement; and
   (e) comparing the first analyte concentration measurement with the at least one additional concentration measurement to confirm that they are within a prescribed percentage of each other.

5. The method of claim 4, further comprising an initial step of incubating the reaction in an open circuit for a predetermined time.

6. The method of claim 4, wherein the initial step of incubating is initiated by adding the sample to the electrochemical cell.

7. A method for obtaining measurements of analytes contained in a sample in order to determine the concentration of analyte in the sample, in a system including reagents incorporated into a sample receiving portion of an electrochemical device that measures the analytes and that has a pair of electrodes including working and counter electrodes, the working and counter electrodes being made of the same electrically conducting materials, the ratio of the surface area of the counter electrode to the surface area of the working electrode being 1:1 or less, the reagents including the oxidized form of a redox mediator, an enzyme, and a buffer, the oxidized form of the redox mediator being capable of receiving at least one electron from a reaction involving enzyme, analyte, and the oxidized form of the redox mediator and being present in sufficient amount to insure that current produced by diffusion limited electrooxidation as a result of the reaction following application of a potential to the working and counter electrodes is limited by the oxidation of the reduced form of the redox mediator at the working electrode surface, the enzyme being present in sufficient amount to catalyze the reaction involving the enzyme, analyte, and the oxidized form of the redox mediator, and the buffer having a higher oxidation potential than the reduced form of the redox mediator and being present in sufficient amount to provide and maintain a pH at which the enzyme catalyzes the reaction involving the enzyme, analyte, and the oxidized form of the redox mediator, comprising:

(a) measuring a first Cottrell current attributable to the diffusion limited electrooxidation at a first predetermined time;

(b) measuring at least one second Cottrell current attributable to the diffusion limited electrooxidation at one or more subsequent predetermined times;

(c) converting the first Cottrell current into a first analyte concentration measurement using a calibration slope and an intercept specific for the at least one second Cottrell current measurement; and (d) comparing the first analyte concentration measurement with the at least one additional concentration measurement to confirm that they are within a prescribed percentage of each other.

8. A method for obtaining measurements of analytes contained in a sample in order to determine the concentration of analyte in the sample, in a system including reagents incorporated into a sample receiving portion of an electrochemical device that measures an analyte and that has a pair of electrodes including working and counter electrodes, the working and counter electrodes being made of the same electrically conducting materials, the ratio of the surface area of the counter electrode to the surface area of the working electrode being 1:1 or less, the reagents including the reduced form of a redox mediator, an enzyme, and a buffer, the reduced form of the redox mediator being capable of donating at least one electron from a reaction involving enzyme, analyte, and the reduced form of the redox mediator and being present in sufficient amount to insure that current produced by diffusion limited electroreduction as a result of the reaction following application of a potential to the working and counter electrodes is limited by the reduction of the oxidized form of the redox mediator at the working electrode surface, the enzyme being present in sufficient amount to catalyze the reaction involving the enzyme, analyte, and the reduced form of the redox mediator, and the buffer having a lower reduction potential than the oxidized form of the redox mediator and being present in sufficient amount to provide and maintain a pH at which the enzyme catalyzes the reaction involving the enzyme, analyte, and the reduced form of the redox mediator, comprising:

(a) measuring a first Cottrell current attributable to the diffusion limited electroreduction at a first predetermined time;

(b) measuring at least one second Cottrell current attributable to the diffusion limited electroreduction at one or more subsequent predetermined times;

(c) converting the first Cottrell current into a first analyte concentration measurement using a calibration slope and an intercept specific for the first Cottrell current measurement;

(d) converting the at least one second Cottrell current reading into an additional analyte concentration using a calibration slope and an intercept specific for the at least one second Cottrell current measurement; and (e) comparing the first analyte concentration measurement with the at least one additional concentration measurement to confirm that they are within a prescribed percentage of each other.

9. The method of claim 8, further comprising an initial step of incubating the reaction in an open circuit for a predetermined time.

10. The method of claim 9, wherein the initial step of incubating is initiated by adding the sample to the electrochemical cell.

* * * * *